United States Patent [19]

Bezwada

[11] 4,228,045

[45] Oct. 14, 1980

[54] METHOD OF ADHESION OF RUBBER TO REINFORCING MATERIALS

[75] Inventor: Rao S. Bezwada, Somerville, N.J.

[73] Assignee: American Cyanamid Company, Stamford, Conn.

[21] Appl. No.: 8,204

[22] Filed: Jan. 31, 1979

[51] Int. Cl.$^2$ .................... C08L 7/00; C08L 11/00
[52] U.S. Cl. ........................... 260/4 R; 260/5; 260/29.4 UA; 260/42.37; 260/784; 525/192; 525/347
[58] Field of Search .......... 260/3.3, 4 R, 5, 29.4 UA, 260/783, 784, 851, 852, 853, 855, 42.37; 525/347, 192

[56] References Cited

U.S. PATENT DOCUMENTS

| | | | |
|---|---|---|---|
| 3,361,617 | 6/1962 | Kaizerman | 260/852 |
| 3,638,702 | 2/1972 | Endter | 260/852 |
| 3,765,836 | 10/1973 | Readshaw et al. | 260/29.4 R X |

*Primary Examiner*—Theodore E. Pertilla
*Attorney, Agent, or Firm*—Frank M. Van Riet

[57] ABSTRACT

A vulcanizable rubber composition comprising a rubber, a vulcanizing agent and glyoxal or a glyoxal reaction product and a method of adhering fiber or steel tire cord, are disclosed.

18 Claims, No Drawings

METHOD OF ADHESION OF RUBBER TO REINFORCING MATERIALS

BACKGROUND OF THE INVENTION

It has been conventional practice to prepare various textile reinforcing fibers, to be used in contact with rubber compositions, by pretreating them with a rubber latex and a phenol-formaldehyde resin, in which the phenol has almost always been resorcinol. This is the so-called "RFL" (Resorcinol-Formaldehyde-Latex) method. Another method commonly used is to generate the resin in situ in the vulcanized rubber-textile matrix by incorporating therein a formaldehyde (or methylene) donor compound, e.g., hexamethylenetetramine or hexamethoxymethylmelamine, and a formaldehyde (or methylene) acceptor compound, e.g., resorcinol. This method has been particularly effective where the reinforcing material is brass-coated steel wire, since pretreatment of the wire by the aforementioned "RFL" method has proven to be largely ineffective. The methylene donor-acceptor method is described by Endter, U.S. Pat. No. 3,517,722.

SUMMARY OF THE INVENTION

It has been found that excellent adhesion of rubber to reinforcing materials, such as textile fibers and steel wire, is achieved by the incorporation into the rubber composition, before vulcanization thereof in the presence of reinforcing materials, of (a) glyoxal, (b) a reaction product of glyoxal and urea, or (c) a reaction product of glyoxal, urea, and formaldehyde, as defined hereinbelow.

Such materials have not been used heretofore in adhesion of textile fibers or steel wire to rubber. Moreover, it is quite surprising that excellent adhesion, equal to or better than that which is obtained by present methods, is achieved by the use of glyoxal alone, since it would seem to deviate from the commonly accepted methylene donor-acceptor theory of adhesion. The method of the present invention has the advantage of achieving adhesion with a one-component, readily obtained promoter system.

DESCRIPTION OF THE INVENTION INCLUDING PREFERRED EMBODIMENTS

As used herein, the term "glyoxal" means commercially available forms of glyoxal including anhydrous, monomeric glyoxal which is described as a low melting (15° C.), low boiling (51° C.) compound. "Glyoxal", also includes aqueous solutions of glyoxal with or without small concentrations of formaldehyde, in that most commercially available glyoxal solutions will contain from about 0.01 to about 0.4 moles of formaldehyde per mole of glyoxal. It is known that when aqueous solutions of glyoxal, of concentrations greater than about 40 percent, are allowed to stand for prolonged periods of time, the hydrated trimer (I) separates as a crystalline product.

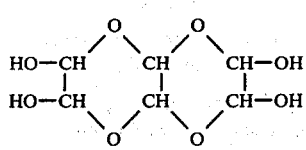

(I)

Simple vacuum distillation or stripping below 100° C. produces a hydrated polymer containing as little as 5 percent water, which corresponds to the polymer of formula (II) wherein n=12 and m=2.

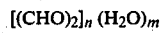

"Glyoxal" may also be considered to be 1,1,2,2-tetrahydroxyethane (III) in equilibrium with smaller amounts of glyoxal dimer (IV) and the timer (I), as follows:

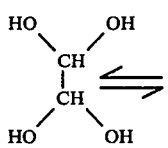

(III)

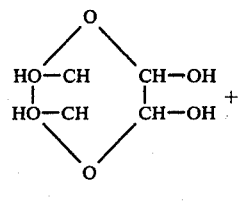

(IV)

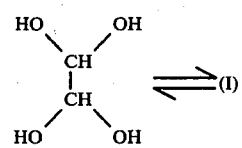

Thus, in accordance with the present invention, any one or more or all of the forms described above alone or in admixture, as well as glyoxal monomer (V), which structure is oftimes set forth in the prior art as representative of glyoxal,

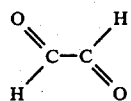

can be used herein.

Reaction products of glyoxal and urea are readily obtained by the condensation of 0.1 to 10, preferably 0.5 to 4, molar proportions, or more, of urea with one molar proportion of glyoxal. The reaction products are ordinarily resinous mixtures. A desirable, and preferred species, of urea/glyoxal reaction product, which may be isolated as a crystalline compound from the reaction mixtures in the presence of water is 4,5-dihydroxyethylene urea (VI), commonly designated DHEU,

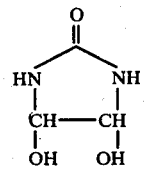

Even more preferred species of glyoxal/urea reaction products are those obtained by reacting glyoxal and urea at mole ratios of 1/1–1/1.5 (from which DHEU may be isolated in the presence of water, as shown in the accompanying examples).

Reaction products of glyoxal, 1-2 moles of urea, and 1-2 moles of formaldehyde are also useful adhesion promoters in accordance with this invention. Preferred species are 1-methylol- and 1,3-dimethylol-4,5-dihydroxy-2-imidazolidinone (VII) and (VIII), respectively, which can be prepared by reacting about 1 mole of DHEU with 1-2 moles of formaldehyde, when the DHEU is recovered as such. Products VII and VIII are also formed, in situ, when the glyoxal, urea and formaldehyde are charged together, as described above.

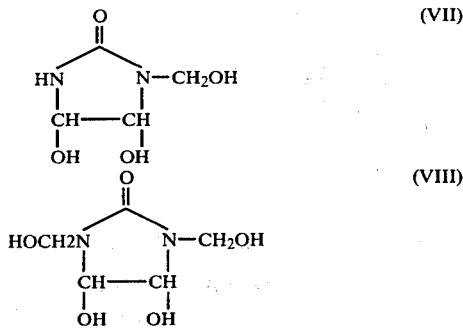

As can be readily appreciated, when a commercially available glyoxal solution which contains formaldehyde as mentioned above is employed as the glyoxal charge with which the urea is reacted, the resultant products will contain small amounts of compounds (VII) and (VIII) as well as ureaglyoxal-formaldehyde resinous mixtures.

It is pointed out, however, that the presence of formaldehyde has a deleterious effect on the physical properties of the vulcanized rubber, although adhesion properties are good. Thus, although reaction products of glyoxal and urea, as described hereinabove, may contain as much as 10 moles of urea per mole of glyoxal, it is disadvantageous to react more than 2 molar proportions of formaldehyde therewith, since the physical properties of the vulcanized rubber to which such products are added are negatively affected thereby. Moreover, optimum adhesion results, with minimum loss in rubber properties, are obtained when glyoxal containing less than about 0.4 moles of formaldehyde, is used.

The improved adhesion promoters of the present invention may be used in bonding reinforcing fibers or wire to rubber used in the manufacture of tires, drive belts, conveyor belts, pressure hoses, and the like. The rubber used may be natural rubber; synthetic diene rubbers, such as polybutadiene, polyisoprene; ethylene-propylene terpolymer rubbers (EPDM); butadiene-styrene copolymer rubbers (SBR); butadiene-acrylomitrile copolymer rubbers (NBR); chloroprene rubber; chlorosulfonated polyethylene; or mixtures thereof.

The reinforcing materials useful herein include textile materials, in the form of fibers or fabric, commonly used to reinforce rubber compositions, which include cotton, rayon, polyamides, polyesters, polyimides, and the like, and metal materials such as wires and cord threads of raw steel, zinc-coated steel and the like. A particularly useful reinforcing material found to form strong adhesive bonds with rubber in accordance with this invention is brass-coated steel wire.

The vulcanizable rubber composition to which the reinforcing materials are bonded during vulcanization contain, in addition to the promoter compound of the invention, other conventional compounding ingredients such as carbon black, antioxidants, sulfur, zinc oxide, accelerators, high surface area silica (including mixtures thereof with carbon black), processing and softening oils, and the like.

The glyoxal or glyoxal reaction product is incorporated into the vulcanizable composition in an amount of from about 1 to 10 parts, by weight, per one hundred parts of weight of rubber used. Preferably, the compounds are used in an amount of from about 2 to 4 parts, by weight, same basis.

For optimum adhesion of the reinforcing material to rubber, particularly when using a metal such as brass-coated steel wire, it has been found desirable to incorporate a high surface area silica into the vulcanizable rubber composition. The reason for enhanced adhesion in the presence of a high surface area silica is speculative, but may result from hydrogen bonding of hydroxyl groups of the silica with the components of the vulcanizable system. The silica is used in an amount of from about 2 to 14 parts, by weight, per hundred parts of rubber, preferably about 8 to 12 parts per hundred of rubber although good adhesion is still achieved in the absence of the silica.

The use of glyoxal, or one of the glyoxal-urea reaction products, is facilitated by first absorbing the liquid onto an inert solid carrier, such as the aforementioned high surface area silica; precipitated, hydrous calcium silicate, and the like, and adding the compound to the rubber as a free-flowing solid.

Adhesion is measured using ASTM D-2229-73 with 15 reinforcing members embedded in a 0.5"×0.5"×8" block of rubber. The force to pull the metal wire or textile fiber out of the rubber is recorded in pounds per linear inch (pli) of embedded length, except that in the table following Example 29, a modification was employed whereby seven alternating reinforcing members are pulled while holding the specimen by the two adjacent wires protruding from the opposite side of the sample (the "Harp" test). This modification has little effect on the recorded adhesion values.

The following examples are provided to illustrate the particular features of the invention. Unless otherwise specified, all parts are by weight.

EXAMPLE A

Preparation of 4,5-Dihydroxyethyleneurea

A 40% glyoxal solution, formaldehyde free, (321 parts; 2.2 moles), is diluted with 107 parts of water to give a 30% solution, and adjusted to pH 7 with 5 N NaOH. While stirring at room temperature, 200 parts (3.34 moles) of prilled urea is added and the mixture stirred at 25°-30° C. for about 2 hours. The reaction mixture is poured into an open tray, and after 2 to 3 hours, crystals form which are filtered, stirred with 160 parts of methanol and filtered again. The crystals are recrystallized from 500 parts of 40% aqueous methanol. There is obtained a yield of 75.5 parts, m.p. 152° C. (dec.) of 4,5-dihydroxyethyleneurea.

EXAMPLE B

Preparation of Glyoxal-Urea Reaction Product (molar ratio 1.0:0.5)

Urea (30 parts, 0.5 mole) and glyoxal (145.1 parts of 40% aqueous solution, formaldehyde free, 1.0 mole), adjusted to pH 7 with 5 N soldium hydroxide, are reacted for about 3 hours at 25°-30° C. The reaction mixture, containing 50.3% solids, is poured into an open tray and permitted to stand open to the atmosphere to evaporate water therefrom. After several hours standing, a composition is obtained containing 78% solids.

EXAMPLES C-K

Following the general procedure of Example 3, glyoxal-urea reaction products are prepared as shown in the following table:

| Example | Glyoxal/Urea (moles) | % Solids |
|---|---|---|
| C | 1.0/1.0 | 74.4 |
| D | 1.0/1.5 | 74.4 |
| E | 1.0/2.0 | 77.7 |
| F | 1.0/2.5 | 88.7 |
| G | 1.0/3.0 | 89.3 |
| H | 1.0/3.5 | 88.6 |
| I | 1.0/4.0 | 84.2 |
| J | 1.0/6.0 | 60.0 |
| K | 1.0/10.0 | 60.0 |

EXAMPLE L

Preparation of Glyoxal-Urea Reaction Product on Hydrous Calcium Silicate (mole ratio 1:0.5)

Urea (60 parts, 1.0 mole) and glyoxal (290 parts of 40% solution containing 5% formaldehyde; 116 parts, 2.0 moles), adjusted to pH 7 with 5 N sodium hydroxide, are reacted for 3 hours at 25°–30° C. The reaction product (140 parts) is absorbed onto 60 parts of precipitated hydrous calcium silicate and the mixture is dried at 70° C. for about 16 hours. The product is passed through a 60 mesh screen. Active urea-glyoxal reaction product is 50 percent.

EXAMPLE M-U

Following the general procedure of Example L, glyoxal-urea-formaldehyde reaction products are prepared as shown in the following table:

| Example | Glyoxal/Urea (moles) | % Active |
|---|---|---|
| M | 1.0/1.0 | 57.5 |
| N | 1.0/1.5 | 62 |
| O | 1.0/2.0 | 63.2 |
| P | 1.0/2.5 | 65.5 |
| Q | 1.0/3.0 | 67.9 |
| R | 1.0/3.5 | 65.3 |
| S | 1.0/4.0 | 65.6 |
| T | 1.0/6.0 | 60 |
| U | 1.0/10.0 | 60 |

EXAMPLE V

Preparation of 1-Methylol-4,5-Dihydroxy-2-Imidazolidinone

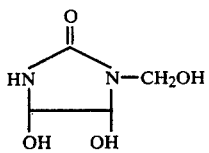

Formaldehyde (8.85 parts of 37.3 percent solution; 0.11 mole), adjusted to pH 7–8.5, is diluted with water (20 parts). While stirring, 11.8 parts (0.1 mole) of dihydroxyethyleneurea powder are added. The temperature is raised to 55° C., held at 55° C. for 30 minutes, cooled to room temperature, and refrigerated. The sample is recovered as an 80 percent aqueous solution.

EXAMPLE W

Preparation of 1,3-Dimethylol-4,5-Dihydroxy-2-Imidazolidinone

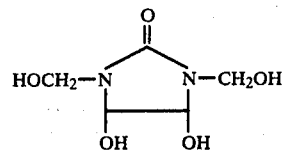

An aqueous solution containing 45 percent by weight of the subject compound, prepared according to the procedure of Chao, U.S. Pat. No. 3,903,033, Example 1, is evaporated to give a solution containing 90 percent by weight of the compound.

A polyblend of natural rubber polybutadiene and a styrene-butadiene (25/75) rubber is compounded as follows and used in the evaluation of the adhesion promoters of the invention:

| Polyblend Masterbatch Formulation | |
|---|---|
| Natural rubber | 52 |
| Polybutadiene | 18 |
| Styrene-butadiene rubber | 30 |
| Carbon black | 40 |
| Zinc oxide | 5 |
| Stearic acid | 2 |
| Reaction product of diphenylamine and acetone; 50 percent active | 2 |
| Silica (high surface area) | 10 |

Similarly, a natural rubber masterbatch is compounded as follows:

| Natural Rubber Masterbatch Formulation | |
|---|---|
| Natural rubber | 100 |
| Carbon black | 40 |
| Zinc oxide | 5 |
| Stearic acid | 2 |
| Reaction product of diphenylamine and acetone; 50 percent active | 2 |
| Silica (high surface area) | 10 |

In the following examples, one or the other of the polyblend or natural rubber masterbatch formulations is used, in each case in an amount containing 100 parts of rubber.

EXAMPLES 1-3

Dihydroxyethyleneurea (DHEU) is evaluated as an adhesion promoter in natural rubber as follows:

| Compositions | Control A | 1 | 2 | 3 |
|---|---|---|---|---|
| Natural rubber masterbatch | 158.5 | 158.5 | 158.5 | 158.5 |
| Sulfur | 3.75 | 3.75 | 3.75 | 3.75 |
| N-oxydiethylene benzothiazole-2-sulfenamide | 0.8 | 0.8 | 0.8 | 0.8 |
| Dihydroxyethyleneurea | — | 1 | 2 | 3 |

The compositions are compounded on a standard rubber mill for 10 minutes at 120° to 175° F., embedded with 15 clean, brass-coated steel wires, placed parallel, and vulcanized at 307° F. Properties are given below:

| Stress-Strain and Adhesion Properties | Control A | 1 | 2 | 3 |
|---|---|---|---|---|
| Modulus @ 300%, psi | 1662 | 1624 | 1660 | 1790 |
| Tensile, psi | 3883 | 3965 | 3676 | 3583 |
| Elongation, % | 541 | 543 | 546 | 501 |
| Adhesion, pli | 127 | 160 | 182 | 225 |

The data illustrate that dihydroxyethyleneurea improves the adhesion of steel wire to rubber.

EXAMPLES 4–12

Glyoxal liquid (containing no formaldehyde; 67.5% aqueous solution) and various urea-glyoxal reaction products made therefrom as shown in Examples B–I, are evaluated as adhesion promoters in natural rubber as follows:

| Compositions | Control B | Comparative | 4 | 5 | 6 | 7 | 8 | 9 | 10 | 11 | 12 |
|---|---|---|---|---|---|---|---|---|---|---|---|
| Natural rubber masterbatch | 158.5 | | | | | | | | | | |
| Sulfur | 3.75 | | | | | | | | | | |
| N-oxydiethylene benzothiazole-2-sulfenamide | 0.8 | | | | | | | | | | |
| Urea | | 3 | | | | | | | | | |
| Glyoxal liq. (67.5%) | | | 3 | | | | | | | | |
| Urea-Glyoxal Products | | | | | | | | | | | |
| 0.5/1 | | | | 3 | | | | | | | |
| 1.0/1 | | | | | 3 | | | | | | |
| 1.5/1 | | | | | | 3 | | | | | |
| 2.0/1 | | | | | | | 3 | | | | |
| 2.5/1 | | | | | | | | 3 | | | |
| 3.0/1 | | | | | | | | | 3 | | |
| 3.5/1 | | | | | | | | | | 3 | |
| 4.0/1 | | | | | | | | | | | 3 |

The compositions are compounded on a standard rubber mill for 10 minutes at 120° to 175° F., embedded with 15 clean, brass-coated steel wires, placed parallel, and vulcanized at 307° F. Properties are given below.

| Stress-Strain and Adhesion Properties | Control | Comparative | 4 | 5 | 6 | 7 | 8 | 9 | 10 | 11 | 12 |
|---|---|---|---|---|---|---|---|---|---|---|---|
| Modulus % 300%, psi | 1848 | 2246 | 1677 | 1868 | 1718 | 1905 | 2103 | 1991 | 2044 | 2138 | 2059 |
| Tensile, psi | 3939 | 3143 | 3796 | 3858 | 3948 | 3858 | 3583 | 3541 | 3446 | 3612 | 3382 |
| Elongation, % | 529 | 392 | 541 | 536 | 560 | 527 | 463 | 483 | 465 | 459 | 443 |
| Adhesion, pli | 182 | 174 | 251 | 220 | 245 | 225 | 236 | 230 | 196 | 216 | 228 |

All of the compositions except the comparative example, which contains only urea, exhibit improved adhesion over Control B.

EXAMPLES 13–21

Glyoxal (40% aqueous solution containing 0.4% formaldehyde) and the urea-glyoxal reaction products of Examples L–S above, obtained therefrom are absorbed onto precipitated, hydrous calcium silicate and incorporated into natural rubber as a free-flowing solid.

| Compositions | % Active* | Control C | 13 | 14 | 15 | 16 | 17 | 18 | 19 | 20 | 21 |
|---|---|---|---|---|---|---|---|---|---|---|---|
| Natural rubber masterbatch | | 158.5 | | | | | | | | | |
| Sulfur | | 3.75 | | | | | | | | | |
| N-oxydiethylene benzothiazole-2-sulfenamide | | 0.8 | | | | | | | | | |
| Glyoxal | | | 3 | | | | | | | | |
| Urea-Glyoxal Reaction Products | | | | | | | | | | | |
| 0.5/1 | 50 | | | 3 | | | | | | | |
| 1.0/1 | 57.5 | | | | 3 | | | | | | |
| 1.5/1 | 62 | | | | | 3 | | | | | |
| 2.0/1 | 63.2 | | | | | | 3 | | | | |
| 2.5/1 | 65.5 | | | | | | | 3 | | | |
| 3.0/1 | 67.9 | | | | | | | | 3 | | |
| 3.5/1 | 65.3 | | | | | | | | | 3 | |
| 4.0/1 | 65.6 | | | | | | | | | | 3 |

*Remainder silicate

The compositions are compounded and vulcanized as described in Examples 4–12. Results are given below.

| Stress-Strain and Adhesion Properties | Control C | 13 | 14 | 15 | 16 | 17 | 18 | 19 | 20 | 21 |
|---|---|---|---|---|---|---|---|---|---|---|
| Modulus @ 300%, psi | 1629 | 1478 | 1516 | 1776 | 1871 | 1935 | 2261 | 2371 | 2308 | 2261 |

-continued

| Stress-Strain and Adhesion Properties | Control C | 13 | 14 | 15 | 16 | 17 | 18 | 19 | 20 | 21 |
|---|---|---|---|---|---|---|---|---|---|---|
| Tensile, psi | 3868 | 3288 | 3360 | 3639 | 3449 | 3557 | 3852 | 3767 | 3763 | 3693 |
| Elongation, % | 533 | 519 | 510 | 507 | 468 | 492 | 485 | 440 | 445 | 466 |
| Adhesion, pli | 172 | 194 | 222 | 216 | 223 | 243 | 230 | 222 | 215 | 216 |

EXAMPLES 22–23

Following the procedure of Examples 13–21, reaction products of urea and glyoxal, prepared at high ratios of urea to glyoxal (Examples T & U) are absorbed onto precipitated, hydrous calcium silicate and evaluated in natural rubber.

| Composition | % Active* | Control D | 22 | 23 |
|---|---|---|---|---|
| Natural rubber masterbatch | | 158.5 | | |
| Sulfur | | 3.75 | | |
| N-oxydiethylene benzothiazole-2-sulfenamide | | 0.8 | | |
| Urea-Glyoxal Reaction Product | | | | |
| 6/1 | 60 | | 3 | |
| 10/1 | 60 | | | 3 |
| Stress-Strain and Adhesion Properties | | | | |
| Modulus @ 300%, psi | | 1776 | 2222 | 2215 |
| Tensile, psi | | 4117 | 3719 | 3646 |
| Elongation, % | | 548 | 461 | 450 |
| Adhesion, pli | | 185 | 223 | 208 |

*remainder silicate

EXAMPLES 24–28

Following the procedure of Examples 13–21, glyoxal on said silicate, and various urea-glyoxal reaction products of Examples M, N, O, and S, absorbed on said silicate, are evaluated in a blend of natural and synthetic rubber.

| Compositions | % Active* | Control E | 24 | 25 | 26 | 27 | 28 |
|---|---|---|---|---|---|---|---|
| Polyblend masterbatch | | 159 | | | | | |
| Sulfur | | 2.4 | | | | | |
| N-oxydiethylene benzothiazole-2-sulfenamide | | 1.25 | | | | | |
| Glyoxal | 49.8 | | 3 | | | | |
| Urea-Glyoxal Products | | | | | | | |
| 1.0/1 | 57.5 | | | 3 | | | |
| 1.5/1 | 62 | | | | 3 | | |
| 2.0/1 | 63.2 | | | | | 3 | |
| 4.0/1 | 65.6 | | | | | | 3 |
| Stress-Strain and Adhesion Properties | | | | | | | |
| Modulus @ 300%, psi | | 1932 | 1695 | 1668 | 1767 | 1805 | 1974 |
| Tensile, psi | | 3204 | 2998 | 3083 | 2809 | 2595 | 2865 |
| Elongation, % | | 423 | 463 | 459 | 415 | 386 | 396 |
| Adhesion, pli | | 117 | 177 | 193 | 188 | 197 | 164 |

*remainder silicate

EXAMPLES 29–31

1-Methylol-4,5-dihydroxy-2-imidazolidinone (MMDHEU; Example V) and 1,3-dimethylol-4,5-dihydroxy-2-imidazolidinone (DMDHEU; Example W) and dihydroxyethyleneurea (DHEU; Example A) are evaluated in a blend of natural and synthetic rubber following the procedure of Examples 24–28.

| Compositions | Control F | 29 | 30 | 31 |
|---|---|---|---|---|
| Polyblend masterbatch | 159 | | | |
| Sulfur | 2.4 | | | |
| N-oxydiethylene benzothiazole-2-sulfenamide | 1.25 | | | |
| DHEU | | 3 | | |
| MMDHEU | | | 3.75 | |
| DMDHEU | | | | 3.5 |
| Stress-Strain and Adhesion Properties | | | | |
| Modulus @ 300%, psi | 1932 | 1921 | 1651 | 1665 |
| Tensile, psi | 3204 | 3089 | 3196 | 3079 |
| Elongation, % | 423 | 416 | 463 | 452 |
| Adhesion, pli | 117 | 223 | 204 | 201 |

EXAMPLE 32

Following the procedure of Examples 1–4, dihydroxyethylene urea is evaluated as an adhesion promoter in natural rubber stock. No silica is used in the natural rubber masterbatch.

| | Control G | 32 |
|---|---|---|
| Natural Rubber Masterbatch | 148.5 | 148.5 |
| Sulfur | 3.75 | 3.75 |
| N-oxydiethylene benzothiazole-2-sulfenamide | 0.8 | 0.8 |
| Dihydroxyethyleneurea | | 3.0 |

The compositions are compounded on a standard rubber mill for 10 minutes at 120°–175° F., embedded with 15 brass-coated steel wires, placed parallel, and vulcanized at 307° F. Properties are given below.

| Stress-Strain and Adhesion Properties | Control G | 32 |
|---|---|---|
| Modulus @ 300%, psi | 1644 | 1698 |
| Tensile, psi | 4250 | 4131 |
| Elongation, % | 558 | 536 |
| Adhesion, pli | 126 | 193 |

The data illustrate the dihydroxyethyleneurea provides improved adhesion in the absence of silica.

EXAMPLES 33-41

When the procedure of Examples 13-41 is again followed except that the Masterbatch is devoid of high surface area silica, results similar to those shown in Example 32 are achieved.

EXAMPLE 42

The procedure of Example 4 is again followed except that the glyoxal solution is replaced by pure anhydrous, monomeric glyoxal and the masterbatch and glyoxal are compounded at a temperature of below 50° C. When the resultant material is tested, similar results are achieved.

EXAMPLE 43

When the glyoxal solution of Example 4 is distilled in vacuo to 5% water and the resultant material is compounded with rubber as set forth therein, excellent results are observed.

What is claimed is:

1. A vulcanizable rubber composition consisting essentially of (A) natural or synthetic rubber, or a mixture thereof; (B) a vulcanizing agent; and (C) from about 1 to 10 parts by weight, per hundred parts by weight of rubber, of (a) glyoxal, (b) a reaction product of glyoxal and from 0.1 to 10 molar proportions of urea or (c) a reaction product of glyoxal, 0.1 to 10 molar proportions of urea and from 0.01 to 2 molar proportions of formaldehyde per molar proportion of glyoxal.

2. A composition according to claim 1 wherein said rubber is natural rubber, polybutadiene, polyisoprene, ethylenepropylene terpolymer rubber, butadiene-styrene copolymer rubber, butadieneacrylonitrile copolymer rubber, chloroprene rubber, chlorosulfonated polyethylene, or mixtures thereof.

3. A composition according to claim 2 wherein said rubber is natural rubber.

4. A composition according to claim 1 wherein said glyoxal compound contains from 0.01 to 0.4 molar proportions of formaldehyde.

5. A composition according to claim 1 containing from 0.1 to 10 molar proportions of urea and from 0.01 to 0.4 molar proportions of formaldehyde per mole proportion of glyoxal.

6. A composition according to claim 1 containing from 0.5 to 4 molar proportions of urea and from 0.01 to 0.4 molar proportions of formaldehyde per molar proportion of glyoxal.

7. A composition according to claim 1 containing from about 1 to 1.5 molar proportions of urea and from 0.1 to 2 molar proportions of formaldehyde per mole proportion of glyoxal.

8. A composition according to claim 1 wherein said (c) is formaldehyde-free, aqueous glyoxal.

9. A composition according to claim 1 wherein said (c) is the reaction product of formaldehyde-free, aqueous glyoxal, and 0.1-10.0 moles of urea.

10. A composition according to claim 9 wherein the molar ratio of said glyoxal and said urea ranges from about 1:1 to about 1:1.5, respectively.

11. A composition according to claim 7, containing 4,5-dihydroxy-2-imidazolidinone.

12. A composition according to claim 7 containing 1-methylol-4,5-dihydroxy-2-imidazolidinone.

13. A composition according to claim 7 containing 1,3-dimethylol-4,5-dihydroxy-2-imidazolidinone.

14. A composition according to claim 1 wherein said (c) is absorbed on an inert solid carrier.

15. A composition according to claim 14 wherein said carrier is hydrous calcium silicate.

16. A composition according to claim 1 wherein said composition additionally comprises (D) from about 2 to 14 parts by weight, per hundred parts by weight of rubber, of a high surface area silica.

17. A composition according to claim 16 wherein said silica comprises 8 to 12 parts per hundred or rubber.

18. A composition according to claim 1 wherein said rubber composition additionally comprises (E) carbon black.

* * * * *